US009775971B2

(12) United States Patent
Hidalgo

(10) Patent No.: US 9,775,971 B2
(45) Date of Patent: Oct. 3, 2017

(54) WRAPS

(71) Applicant: Patches Duana Hidalgo, Woodburn, OR (US)

(72) Inventor: Patches Duana Hidalgo, Woodburn, OR (US)

(*) Notice: Subject to any disclaimer, the term of this patent is extended or adjusted under 35 U.S.C. 154(b) by 165 days.

(21) Appl. No.: 14/638,948

(22) Filed: Mar. 4, 2015

(65) Prior Publication Data
US 2015/0250985 A1 Sep. 10, 2015

Related U.S. Application Data

(60) Provisional application No. 61/947,966, filed on Mar. 4, 2014.

(51) Int. Cl.
A61M 25/02 (2006.01)

(52) U.S. Cl.
CPC ..... A61M 25/02 (2013.01); A61M 2025/0206 (2013.01); A61M 2025/026 (2013.01); A61M 2025/0213 (2013.01); A61M 2025/0266 (2013.01)

(58) Field of Classification Search
CPC .......... A61M 25/02; A61M 2025/0206; A61M 2025/0213; A61M 2025/0266; A61M 2025/026
See application file for complete search history.

(56) References Cited

U.S. PATENT DOCUMENTS

| 3,561,442 A * | 2/1971 | Goswitz | A61F 5/03 128/DIG. 15 |
| 4,470,410 A * | 9/1984 | Elliott | A61M 5/52 128/877 |
| 4,578,062 A * | 3/1986 | Schneider | A41D 13/1245 128/DIG. 26 |
| 4,582,508 A * | 4/1986 | Pavelka | A61M 25/02 128/DIG. 6 |
| 4,666,432 A * | 5/1987 | McNeish | A61M 25/02 128/DIG. 26 |
| 4,799,923 A * | 1/1989 | Campbell | A61M 25/02 128/DIG. 26 |
| 5,038,779 A * | 8/1991 | Barry | A41D 13/0058 2/102 |

(Continued)

OTHER PUBLICATIONS

Healthfully Healing, Pediatric Central Line Protector, Nov. 10, 2012, 1 page, http://web.archive.org/web/20121110082528/http://healthfullyhealing.com/medical/products.

(Continued)

Primary Examiner — Andrew Gilbert
(74) Attorney, Agent, or Firm — Kolisch Hartwell, P.C.

(57) ABSTRACT

Wraps configured to cover a user's body portion having a tube that is at least partially external the user's body and that is in fluid communication with one or more internal systems of the user's body are disclosed. The wraps may include a fabric panel sized and shaped to wrap around and cover the user's body portion. The wraps may additionally include a coupling assembly connected to the fabric panel and configured to secure the fabric panel to one or more portions of the user when the fabric panel is wrapped around the user's body portion. The wraps may further include a holder assembly configured to secure a portion of the tube to the fabric panel.

14 Claims, 3 Drawing Sheets

(56) References Cited

U.S. PATENT DOCUMENTS

| | | | | |
|---|---|---|---|---|
| 5,048,512 A * | 9/1991 | Turner | ................ | A61J 15/0015 128/876 |
| 5,271,745 A * | 12/1993 | Fentress | ................ | A61M 25/02 128/DIG. 26 |
| 5,403,285 A * | 4/1995 | Roberts | ................ | A61M 25/02 604/179 |
| 5,676,294 A * | 10/1997 | Eklund | ................ | A61M 5/1415 128/DIG. 6 |
| D393,310 S * | 4/1998 | Russo | ................ | D24/128 |
| 5,755,698 A * | 5/1998 | Kagan | ................ | A61M 25/02 128/DIG. 26 |
| 5,776,105 A * | 7/1998 | Corn | ................ | A61M 5/1483 604/174 |
| 5,806,096 A * | 9/1998 | Pennington | ................ | A41B 13/08 2/102 |
| 5,897,519 A * | 4/1999 | Shesol | ................ | A61M 25/02 602/75 |
| 6,032,289 A * | 3/2000 | Villapiano | ................ | A41D 13/1245 2/102 |
| 6,206,854 B1 * | 3/2001 | Weaver | ................ | A41D 13/1245 128/DIG. 26 |
| 6,336,458 B1 * | 1/2002 | Nafziger | ................ | A41D 13/1245 128/846 |
| 6,461,319 B1 * | 10/2002 | Ekey | ................ | A61F 13/146 602/62 |
| 6,681,404 B1 * | 1/2004 | Adlard | ................ | A41D 13/1245 2/94 |
| 7,201,739 B2 * | 4/2007 | Walborn | ................ | A61M 25/02 604/178 |
| D544,095 S * | 6/2007 | McLaughlin | ................ | D24/118 |
| 7,738,965 B2 * | 6/2010 | Phillips | ................ | A61N 1/08 224/604 |
| 8,220,079 B2 | 7/2012 | Syska et al. | | |
| 2005/0033241 A1 * | 2/2005 | Hottinger | ................ | A61M 25/02 604/179 |
| 2009/0054844 A1 * | 2/2009 | Alyea | ................ | A41D 13/1245 604/179 |
| 2011/0023208 A1 * | 2/2011 | Liao | ................ | A41D 13/1245 2/102 |
| 2015/0040921 A1 | 2/2015 | Craig | | |
| 2017/0100130 A1 * | 4/2017 | Lakkireddy | ................ | A41D 13/1245 |

OTHER PUBLICATIONS

Carealine Products, PICC Line Sleeve Adult 2 pack, May 2, 2013, 2 pages, http://web.archive.org/web/20130502015537/http://www.carealine.com/all-products/picc-line-sleeve-adult-2-pack/?.

* cited by examiner

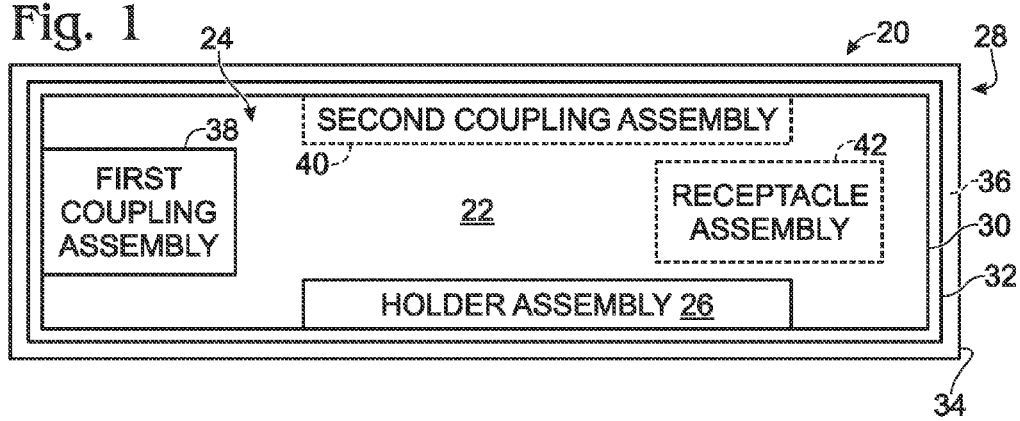
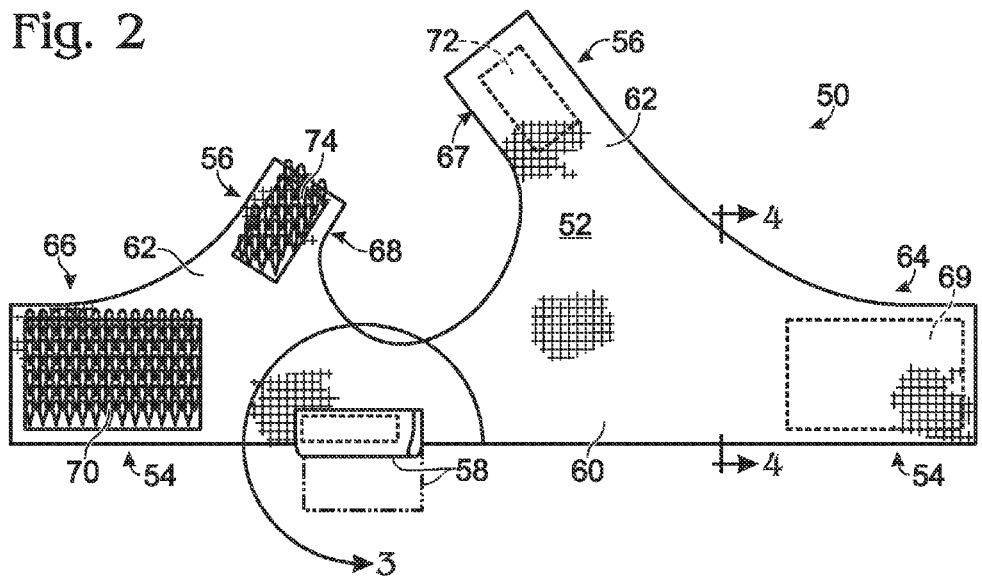
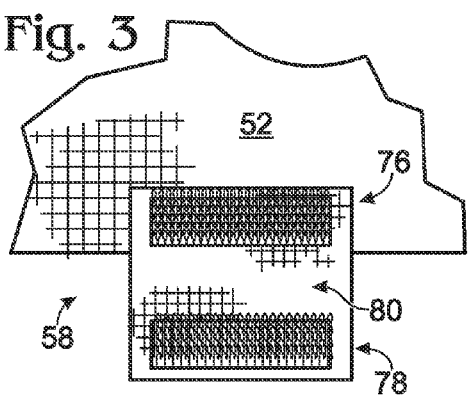
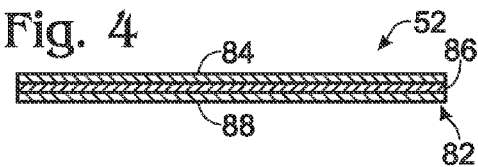
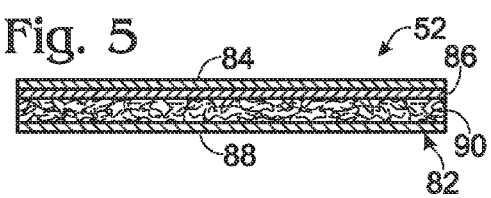

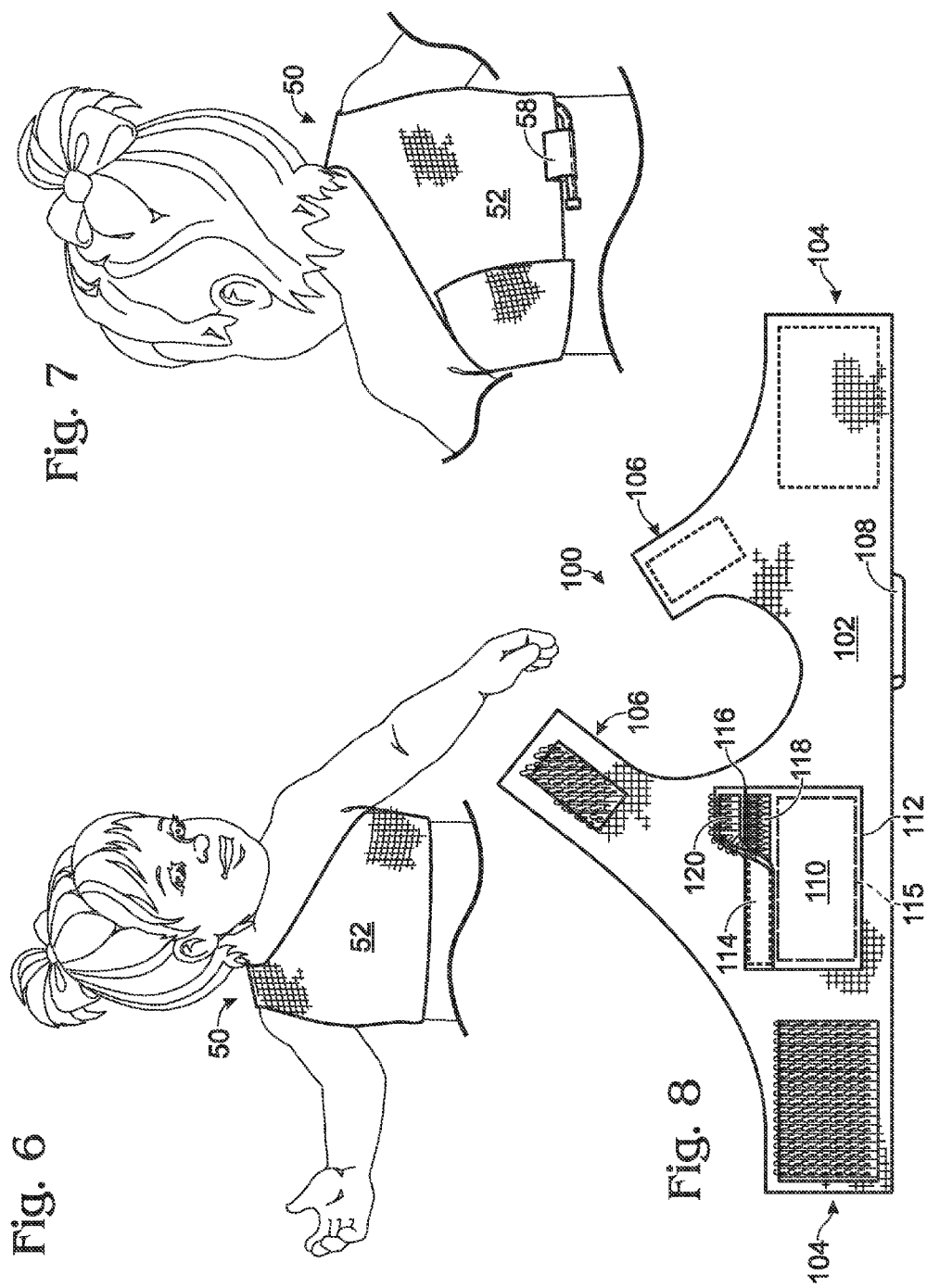

WRAPS

CROSS-REFERENCE TO RELATED APPLICATIONS

This application claims the benefit of U.S. Provisional Patent Application Ser. No. 61/947,966, which was filed on Mar. 4, 2014 and entitled "Lil Hugz Wrap." The complete disclosure of the above application is hereby incorporated by reference for all purposes.

BACKGROUND OF THE DISCLOSURE

Various access devices may be used to provide access to a patient's internal systems (such as cardiovascular system, endocrine system, respiratory system, excretory system, digestive system, etc.) from outside the patient's body. For example, a central venous access device, such as a PORT-A-CATH® device, may be installed beneath the skin of a patient. The central venous access device includes a portal having a septum, and a catheter that runs from the portal and is surgically inserted into a vein. The septum is made of a special self-sealing silicone rubber that may be punctured hundreds of times before it weakens significantly. A health professional may puncture the septum with a needle through the skin of the patient to gain access to the central venous access device to deliver medicine, deliver nutrition, or withdraw blood.

Covers may be used to protect surgically implanted central venous access devices when not in use or accessed. Examples of those covers are described in U.S. Pat. No. 8,220,079 and U.S. Patent Application Publication No. 2015/0040921. The complete disclosures of the above references are hereby incorporated by reference for all purposes Another example of an access device is a peripherally inserted central catheter (i.e., PICC or PIC line) that is inserted in a peripheral vein in the arm of a patient and then advanced toward the heart through increasingly larger veins, until the tip rests in the distal superior vena cave or cavoatrial junction of the patient. The area in which the PIC line is inserted through the skin of the patient and in a peripheral vein of the patient may sometimes be referred to as an "insertion site" of the patient's body. A catheter tail (typically with a cap) stays external the patient's arm for access by a health professional, such as to deliver medicine, deliver nutrition, or withdraw blood.

When such access devices are used, there may be some portions of the device that are external to the patient's body. For example, the PICC includes a catheter tail or tube that extends out of the patient's arm. Even when the access devices are substantially (or completely) internal, use of those devices requires one or more tubes (or tubing) that are partially or completely external to the patient's body. For example, a tube or tubing is normally attached to the needle that is used to puncture through the skin and the septum of a central venous access device to provide a passage for delivery of the medicine or nutrition, or for withdrawing blood. The area in which the needle punctures through the skin of the patient and into the septum may be referred to as an "insertion site" of the patient's body.

Instead of puncturing the septum with the needle before every use, some health professional or patients may choose to leave the needle and tubing connected to the central venous access device for future use. This sometimes may be referred to as maintaining "access" to the central venous access device.

Having tubes and/or other components external to a patient's body may be problematic for certain types of patients, such as infants, toddlers, mentally disabled patients, and elderly patients. For example, those patients may push, pull, and/or otherwise manipulate the external components, which may result in loss of access, infection, and/or other complications.

SUMMARY OF THE DISCLOSURE

Some embodiments provide a wrap configured to cover a user's body portion having a tube that is at least partially external the user's body and that is in fluid communication with one or more internal systems of the user's body. In some examples, the wrap includes a fabric panel sized and shaped to wrap around and cover the user's body portion. The wrap additionally includes a coupling assembly connected to the fabric panel and configured to secure the fabric panel to one or more portions of the user when the fabric panel is wrapped around the user's body portion. The wrap further includes a holder assembly configured to secure a portion of the tube to the fabric panel.

Some embodiments provide a wrap configured to cover a user's chest having a tube that is at least partially external the user's body and that is in fluid communication with one or more internal systems of the user's body. In some examples, the wrap includes a fabric panel having a base portion sized and shaped to wrap around and cover the user's chest and a single shoulder portion sized and shaped to wrap around the user's shoulder, the base portion including first and second end portions and the shoulder portion including third and fourth end portions. The wrap additionally includes a first coupling assembly configured to secure the base portion around the user's chest, the first coupling assembly including one of a plurality of hooks and a plurality of corresponding loops attached to the first end portion and the other of a plurality of hooks and a plurality of corresponding loops attached to the second end portion.

The wrap further includes a second coupling assembly configured to secure the shoulder portion around the user's shoulder, the second coupling assembly including one of a plurality of hooks and a plurality of corresponding loops attached to the third end portion and the other of a plurality of hooks and a plurality of corresponding loops attached to the fourth end portion. The wrap additionally includes a holder assembly configured to secure a portion of the tube to the base portion adjacent to the user's back and opposed to the user's chest when the base portion is wrapped around the user's chest, the holder assembly including a fabric strip attached to, or formed with, the fabric panel, the fabric strip having fifth and sixth end portions and a middle portion disposed between the fifth and sixth end portions, the middle portion being configured to support the portion of the tube, the fifth end portion being attached to, or formed with, the base portion and having one of a plurality of hooks and a plurality of corresponding loops, and the sixth end portion having the other of a plurality of hooks and a plurality of corresponding loops.

Some embodiments provide a wrap configured to cover a user's arm having a tube that is at least partially external the user's body and that is in fluid communication with one or more internal systems of the user's body. In some examples, the wrap includes a fabric panel sized and shaped to wrap around and cover the user's arm, the fabric panel including first and second end portions. The wrap additionally includes a coupling assembly configured to secure the fabric panel around the user's arm, the coupling assembly including one of a plurality of hooks and a plurality of corresponding loops attached to the first end portion and the other of a plurality of hooks and a plurality of corresponding loops attached to the second end portion. The wrap further includes a holder assembly configured to secure a portion of the tube to the base portion adjacent to the user's triceps and opposed to the user's biceps when the base portion is wrapped around the user's arm, the holder assembly including a fabric strip attached to, or formed, with, the fabric panel, the fabric strip having third and fourth end portions and a middle portion disposed between the third and fourth end portions, the middle portion being configured to support the portion of the tube, the third end portion being attached to, or formed with, the base portion and having one of a plurality of hooks and a plurality of corresponding loops, and the fourth end portion having the other of a plurality of hooks and a plurality of corresponding loops.

BRIEF DESCRIPTION OF THE DRAWINGS

FIG. 1 is a block diagram of an example of a wrap.

FIG. 2 is a front view of an example of the wrap of FIG. 1.

FIG. 3 is a partial view of the wrap of FIG. 2 showing a holder assembly in an open position.

FIG. 4 is a sectional view of the wrap of FIG. 2 taken along lines 4-4 in FIG. 2.

FIG. 5 is the section view of FIG. 4 shown with an additional padding layer.

FIG. 6 is a front view of person with the wrap of FIG. 2 attached to the person.

FIG. 7 is a rear view of the person of FIG. 6 with the wrap of FIG. 2 attached to the person.

FIG. 8 is a rear view of another example of the wrap of FIG. 1, shown with a receptacle assembly.

DETAILED DESCRIPTION OF THE DISCLOSURE

Figure 9:
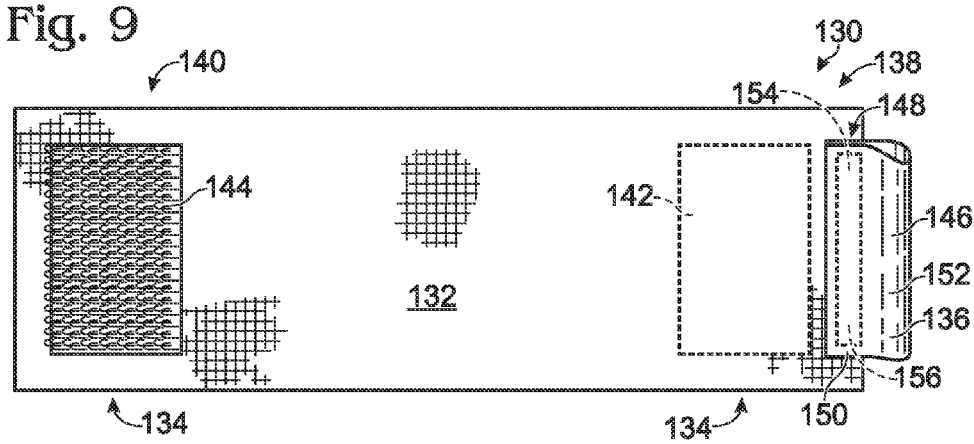
FIG. 9 is a front view of another example of the wrap of FIG. 1.

FIG. 1 shows an example of a wrap 20, which may include any suitable structure configured to cover a user's body portion having an insertion site and a tube that is at least partially external the user's body and that is in fluid communication with one or more internal systems of the user's body. The user's body portion may be any suitable body portion, such as a chest, an arm, a leg, a back, an abdomen, etc. The internal systems may include any suitable internal systems, such as a cardiovascular system, an endocrine system, a respiratory system, an excretory system, a digestive system, etc.

For example, wrap 20 may include a fabric panel 22, a coupling assembly 24, and a holder assembly 26. Fabric panel 22 may include any suitable structure sized and shaped to wrap around and/or cover the user's body portion. The fabric panel may be any suitable size(s) and/or shape(s) configured to wrap around and/or cover the user's body portion. For example, when the user's body portion is the user's chest, the fabric panel may be sized and shaped to wrap around the user's chest and/or the user's shoulder (or both of the user's shoulders). Alternatively, when the user's body portion is the user's arm, the fabric panel may be sized and shaped to wrap around the user's arm. Moreover, when the user's body portion is the user's abdomen, the fabric panel may be sized and shaped to wrap around the user's abdomen.

Fabric panel 22 may include a plurality of layers 28 that are sewn or otherwise attached together. For example, layers 28 may include an outer layer 30, a middle layer 32, and an inner layer 34. The middle layer may be disposed between the outer and inner layers.

Layers 28 may be made of any suitable material(s). For example, outer layer 30 may include one or more cotton materials (such as muslin materials) and/or one or more fleece materials. Additionally, middle layer 32 may include one or more sturdy materials configured to prevent the user from accessing the covered user's body portion through layers 28. For example, middle layer 32 may include one or more wool materials and/or one or more fleece materials. Moreover, inner layer 34 may include one or more materials configured to keep moisture away from the user's body portion, such as one or more wicking fabric materials.

In some examples, layers 28 may include one or more padding layers 36 configured to insulate and/or cushion the user's body portion. The padding layers may be sized about the same as the other layers, such as one or more of the outer, middle, and inner layers. Alternatively, one or more of the padding layers may be sized about the same size or slightly larger than the area of the user's body portion, such as about the same size or slightly larger than the insertion site and/or the interface between the external portion of the tube and the inner portion of the tube (or other internal connection point).

Coupling assembly 24 may be connected to fabric panel 22 and may be configured to secure the fabric panel to one or more portions of the user, such as when the fabric panel is wrapped around the user's body portion. For example, coupling assembly 24 may include hooks, clips, straps, brackets, adjusting (or adjustable) brackets, snap buttons, various traditional sewing notions, hook and eye sets (e.g., those used for brassiere attachment across a user's back), ring and strap sets (e.g., those used for lingerie shoulder straps), detachable grips (e.g., those used to secure nylons to garter belts), spring clips (e.g., those used for barrettes and hair pins), elastic straps, buckles, ribbon ties and cord stops, clips, snaps, curved or straight safety pins, buttons, magnets, zippers, hook-and-loop closure material (such as Velcro® material), and any suitable combination(s) of the above.

Coupling assembly 24 may, for example, include a first coupling assembly 38. In some examples, coupling assembly 24 also may include a second coupling assembly 40. The first and/or second coupling assemblies may include one or more of the above described structures. In some examples, the first and second coupling assemblies may use the same type of structures. In other examples, the first and second coupling assemblies may use different types of structures. Although coupling assembly 24 is shown to include first coupling assembly 38 and, in some examples, second coupling assembly 40, the coupling assembly may include additional coupling assemblies, such as third, fourth, and/or fifth coupling assemblies.

Holder assembly 26 may include any suitable structure configured to secure a portion of the tube (or tubing) to fabric panel 22. The holder assembly may be attached to, of formed with, the fabric panel. In some examples, the holder assembly may be positioned on the fabric panel to minimize access by the user, such as to keep the secured portion of the tube away from the user. For example, when the user's body portion is the user's chest, the holder assembly may be positioned on the fabric panel such that the holder assembly is configured to secure the portion of the tube adjacent to the user's back and opposed to the user's chest when the fabric panel is wrapped around the user's chest. Alternatively, when the user's portion is the user's arm, the holder assembly may be positioned on the fabric panel such that the holder assembly is configured to secure the portion of the tube adjacent the user's triceps and opposed to the user's biceps when the fabric panel is wrapped around the user's arm.

In some examples, wrap 20 may include a receptacle assembly 42, which may include any suitable structure configured to receive an ice pack, a vibration mechanism, a sensor, and/or other similar structure. The receptacle assembly may be attached to, or formed with, fabric panel 22. When fabric panel 22 includes a plurality of layers 28, the receptacle assembly may be attached to, or formed with, for example, inner layer 24 (and/or one or more other layers 28). The receptacle assembly may be positioned in any suitable portion(s) of the fabric panel, such as one or more portion(s) where the insertion site and/or tube will be adjacent to when the fabric panel is wrapped around the user's body portion. Although receptacle assembly 42 is shown to be located on a right portion of the fabric panel in FIG. 1, the receptacle assembly may be in any suitable portion(s) of the fabric panel.

FIG. 2 shows an example of wrap 20, which is generally indicated at 50. Unless explicitly stated, wrap 50 may include one or more components of the other wraps described in the present disclosure. Wrap 50 may include a fabric panel 52, a first coupling assembly 54, a second coupling assembly 56, and a holder assembly 58.

The fabric panel may include a base portion 60 and a shoulder portion 62. The base portion may be sized and shaped to wrap around and/or cover, for example, the user's chest. Base portion 60 may include a first end portion 64 and a second end portion 66 opposed to the first end portion.

The shoulder portion may be attached to, or formed with, the base portion and/or may be sized and shape to wrap around and/or cover, the user's shoulder. Shoulder portion 62 may include a third end portion 67 and a fourth end portion 68 opposed to the third end portion. In some examples, fabric panel 52 may include a single shoulder portion 62. In other examples, the fabric panel may include two shoulder portions (not shown). Although a single right shoulder portion 62 is shown, the fabric panel may alternatively include a single left shoulder portion 62 (not shown).

First coupling assembly 54 may include any suitable structure configured to secure the base portion around the user's chest. For example, the first coupling assembly may include a plurality of hooks 69 and a plurality of corresponding loops 70 (e.g., Velcro® material), which may be attached to any suitable portions of the base portion. For example, the plurality of hooks may be attached to first end portion 64 and the plurality of corresponding loops may be attached to second end portion 66, or vice-versa. Although first coupling assembly 54 is shown and described to include hooks and loops, the first coupling assembly may alternatively, or additionally, include other structure as described above.

Second coupling assembly 56 may include any suitable structure configured to secure the shoulder portion around the user's shoulder. For example, the second coupling assembly may include a plurality of hooks 72 and a plurality of corresponding loops 74 (e.g., Velcro® material), which may be attached to any suitable portions of the shoulder portion. For example, the plurality of hooks may be attached to third end portion 67 and the plurality of corresponding loops may be attached to fourth end portion 68, or vice-versa. Although second coupling assembly 56 is shown and described to include hooks and loops, the second coupling assembly may alternatively, or additionally, include other structure as described above.

FIG. 3 shows an example of holder assembly 58, which may include any suitable structure configured to secure a portion of the tube to the base portion. For example, the holder assembly may include a fifth end portion 76, a sixth end portion 78, and a middle portion 80 disposed between the fifth and sixth end portions. Fifth end portion may be attached to, or formed with, the fabric panel, such as the base portion. Sixth end portion 78 may be opposed from the fifth end portion. The middle portion may be configured to support the portion of the tube.

Although holder assembly 58 is shown to be in a particular position on fabric panel 52, the holder assembly may be in any suitable position(s) on the fabric panel. Additionally, although holder assembly is shown to have a horizontal orientation in FIGS. 2-3, the holder assembly may alternatively have a vertical or diagonal orientation. Moreover, although wrap 50 is shown to include a single holder assembly, the wrap may include two or more holder assemblies, which may be in different positions on the fabric panel and/or in different orientations.

FIG. 4 shows an example of fabric panel 52 having a plurality of layers 82, including an outer layer 84, a middle layer 86, and an inner layer 88. The layers may be made of any suitable materials, as described above.

FIG. 5 shows another example of fabric panel 52 having one or more padding layers 90. Although a single padding layer 90 is shown, the fabric panel may have two or more padding layers. Moreover, although padding layer 90 is shown disposed between middle layer 86 and inner layer 88, the padding layer may alternatively, or additionally, be between any two suitable layers, such as between outer layer 84 and middle layer 86. The layers may be made of any suitable materials, as described above.

FIGS. 6-7 show an example of using wrap 50. Wrap 50 may be wrapped around the user's chest and shoulder covering the user's body portion having the insertion site and/or the external tube. The wrap may be secured using the coupling assemblies, such as by moving end portions of the base portion toward each other to engage the hooks with the corresponding loops, and by moving end portions of the shoulder portion toward each other to engage the hooks with the corresponding loops. A portion of the tube may be secured to the fabric panel by opening the fabric strip (holder assembly), placing the portion of the tube on the middle portion, and moving the end portions of the fabric strip toward each other to engage the hooks with the corresponding loops. The tube may then be located adjacent the user's back and opposed to the user's chest, which may prevent or minimize access to the tube by the user.

FIG. 8 shows another example of wrap 20, which is generally indicated at 100. Unless explicitly excluded, wrap 100 may include one or more components of the other wraps described in the present disclosure. Wrap 100 may include a fabric panel 102, a first coupling assembly 104, a second coupling assembly 106, a holder assembly 108, and a receptacle assembly 110.

Receptacle assembly 110 may include any suitable structure configured to receive, for example, an ice pack and/or other structure. For example, receptacle 110 may include a pocket 112 and a flap 114. Pocket 112 may be sized and shaped to accommodate, for example, an ice pack 115. The pocket may include an opening 116 to receive the ice pack and/or other structure. Flap 114 may be sized and shape to cover opening 116. Pocket 112 may include a plurality of loops 118 and flap 114 may include a plurality of corresponding hooks 120, or vice versa. Alternatively, or additionally, pocket 112 and/or flap 114 may include one or more other closure structures, such as described above.

FIG. 9 shows a further example of wrap 20, which is generally indicated at 130. Unless explicitly excluded, wrap 130 may include one or more components of the wraps described in the present disclosure. Wrap 130 may include a fabric panel 132, a coupling assembly 134, and a holder assembly 136.

Fabric panel 132 may include a first end portion 138 and a second end portion 140 opposed from the first end portion. Coupling assembly 134 may include a plurality of loops 142 and a plurality of corresponding hooks 144, which may be attached to any suitable portions of the fabric panel. For example, plurality of loops 142 may be attached to first end portion 138 and plurality of corresponding hooks may be attached to second end portion 140. Alternatively, or additionally, coupling assembly 134 may include one or more of the closure structures described above.

Holder assembly 136 may include a fabric strip 146 having a third end portion 148, a fourth end portion 150, and a middle portion 152 disposed between the third and fourth end portions configured to support a portion of the tube. The third end portion may include a plurality of hooks 154, and the fourth end portion may include a plurality of corresponding loops 156, or vice-versa. Alternatively, or additionally, the third and fourth end portions may include one or more of the closure structures described above.

Figure 10:
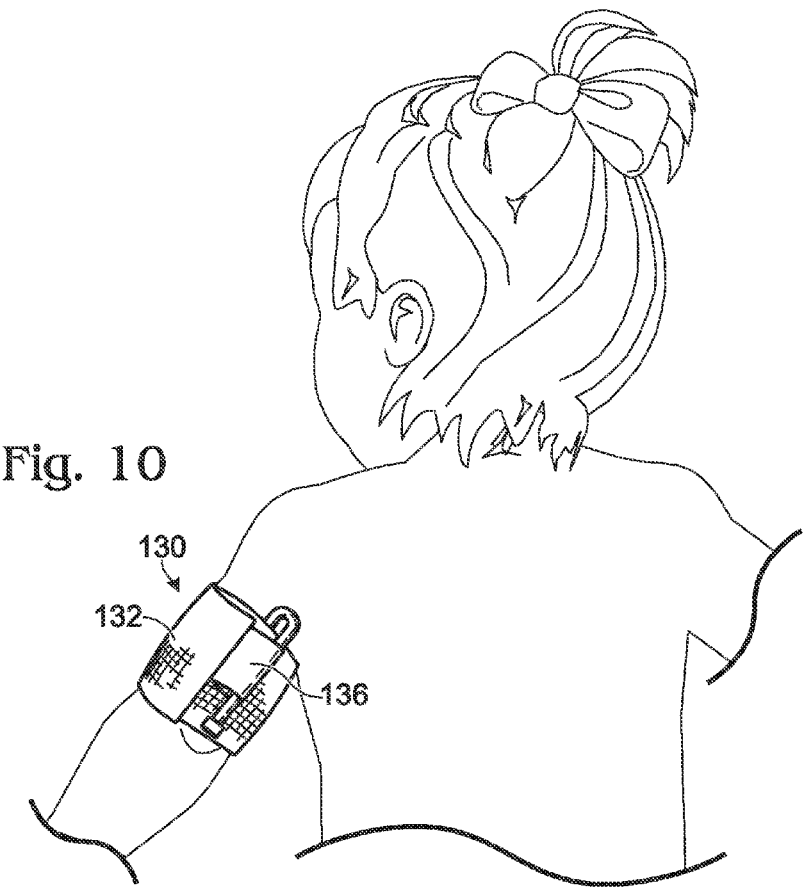
FIG. 10 is a rear view of a person with the wrap of FIG. 9 attached to the person.

FIG. 10 shows an example of use of wrap 130. Wrap 130 may be wrapped around the user's arm covering the user's body portion having the insertion site and/or the external tube. The wrap may be secured using the coupling assembly, such as by moving end portions of the fabric panel toward each other to engage the hooks with the corresponding loops. A portion of the tube may be secured to the fabric panel by opening the fabric strip (holder assembly), placing the portion of the tube on the middle portion, and moving the end portions of the fabric strip toward each other to engage the hooks with the corresponding loops. The tube may then be located adjacent the user's triceps and opposed to the user's biceps, which may prevent or minimize access to the tube by the user.

Although particular examples of wrap 20 are shown and described above, the present disclosure includes other variations of wrap 20. For example, wrap 20 may include the wrap of FIG. 2 attached to and/or formed with the wrap of FIG. 9. Alternatively, wrap 20 may be in the form of a sleeveless or sleeved shirt with one or more holder assemblies to accommodate different tube positions or orientations.

The disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where any claim recites "a" or "a first" element or the equivalent thereof, such claim should be understood to include incorporation of one or more such elements, neither requiring nor excluding two or more such elements.

Inventions embodied in various combinations and subcombinations of features, functions, elements, and/or properties may be claimed through presentation of new claims in a related application. Such new claims, whether they are directed to a different invention or directed to the same invention, whether different, broader, narrower or equal in scope to the original claims, are also regarded as included within the subject matter of the inventions of the present disclosure.

What is claimed is:

1. A wrap configured to cover a user's chest having a tube that is at least partially external the user's body and that is in fluid communication with one or more internal systems of the user's body, the wrap comprising:
    an annular panel configured to wrap around a user's chest, the annular panel including a front portion and a back portion, the front portion being configured to cover the user's chest and the back portion being configured to cover the user's upper back, the front portion including a first end portion and the back portion including a second end portion, the first and second end portions being configured to be disposed adjacent to each other when the annular panel is wrapped around the user's chest;
    a front shoulder panel extending from the front portion of the annular panel and a back shoulder panel extending from the back portion of the annular panel, the front and back shoulder panels being configured to wrap around either a left shoulder or a right shoulder of the user, but not both shoulders simultaneously, the front shoulder panel including a third end portion and the back shoulder panel including a fourth end portion, the third and fourth end portions being configured to be disposed adjacent to each other at an apex of the user's shoulder when the shoulder panel is wrapped around the respective left or right shoulder of the user;
    a first coupling assembly configured to secure the annular panel around the user's chest, the first coupling assembly including a first fastener disposed on the first end portion and a complementary second fastener disposed on the second end portion, wherein the first and second fasteners are configured to releasably attach to each other;
    a second coupling assembly configured to secure the front and back shoulder panels around the respective left or right shoulder of the user, the second coupling assembly including a third fastener disposed on the third end portion and a complementary fourth fastener disposed on the fourth end portion, wherein the third and fourth fasteners are configured to releasably attach to each other adjacent an apex of the user's shoulder when the front and back shoulder panels are wrapped around the respective left or right shoulder of the user; and
    a holder assembly disposed on a lower edge of the back portion of the annular panel and configured to secure a portion of the tube.

2. The wrap of claim 1, wherein the first fastener is one of a plurality of hooks and a plurality of corresponding loops and the second fastener is the other of a plurality of hooks and a plurality of corresponding loops.

3. The wrap of claim 2, wherein the third fastener is one of a plurality of hooks and a plurality of corresponding loops and the fourth fastener is the other of a plurality of hooks and a plurality of corresponding loops.

4. The wrap of claim 1, wherein the holder assembly includes a fabric strip attached to, or formed with, the back portion of the annular panel, the fabric strip having fifth and sixth end portions and a middle portion disposed between the fifth and sixth end portions, the middle portion being configured to support the portion of the tube.

5. The wrap of claim 4, wherein the fifth end portion is attached to, or formed with, the annular panel and includes one of a plurality of hooks and a plurality of corresponding loops, and the sixth end portion includes the other of a plurality of hooks and a plurality of corresponding loops.

6. The wrap of claim 1, wherein the annular panel further includes a pocket configured to support an ice pack, the pocket having an opening to receive an ice pack.

7. The wrap of claim 6, wherein the pocket includes one of a plurality of hooks and a plurality of corresponding loops, the annular panel further including a flap sized and shaped to cover the opening and having the other of a plurality of hooks and a plurality of corresponding loops.

8. The wrap of claim 7, wherein the annular panel includes an outer layer, an inner layer, and a middle layer disposed between the outer and inner layers, and the pocket is formed with, or attached to, the inner layer.

9. The wrap of claim 1, wherein the annular panel includes a plurality of layers including an outer layer, an inner layer, and a middle layer disposed between the outer and inner layers.

10. The wrap of claim 9, wherein the outer layer includes one or more of cotton materials and fleece materials, the inner layer includes one or more wicking fabric materials, and the middle layer includes one or more of wool materials and fleece materials.

11. The wrap of claim 9, wherein the plurality of layers further includes one or more padding layers.

12. The wrap of claim 11, wherein the one or more padding layers are sized about the same as at least one of the outer, middle, and inner layers.

13. A wrap configured to cover a user's chest having a tube that is at least partially external the user's body and that is in fluid communication with one or more internal systems of the user's body, the wrap comprising:
an annular panel having a base portion sized and shaped to wrap around and cover the chest and upper back of the user and a shoulder portion sized and shaped to wrap around either a left shoulder or a right shoulder of the user, but not both shoulders simultaneously, the base portion including first and second end portions and the shoulder portion including third and fourth end portions, the first and second end portions being configured to at least partially overlap each other when the base portion is wrapped around the chest and upper back of the user, the third and fourth end portions being configured to at least partially overlap each other adjacent an apex of the user's shoulder when the shoulder portion is wrapped around the respective left or right shoulder of the user;
a first coupling assembly configured to secure the base portion around the user's chest, the first coupling assembly including a first fastener disposed on the first end portion and a complementary second fastener disposed on the second end portion, wherein the first and second fasteners are configured to releasably attach to each other;
a second coupling assembly configured to secure the shoulder portion around the respective left or right shoulder of the user, the second coupling assembly including a third fastener disposed on the third end portion and a complementary fourth fastener disposed on the fourth end portion, wherein the third and fourth fasteners are configured to releasably attach to each other; and
a holder assembly disposed on a lower edge of the base portion of the annular panel and configured to secure a portion of the tube, the holder assembly including a fabric strip attached to, or formed with, the base portion, the fabric strip having fifth and sixth end portions and a middle portion disposed between the fifth and sixth end portions, the middle portion being configured to support the portion of the tube, the fifth end portion being attached to, or formed with, the base portion and having one of a plurality of hooks and a plurality of corresponding loops, and the sixth end portion having the other of a plurality of hooks and a plurality of corresponding loops.

14. A wrap configured to cover a user's chest having a tube that is at least partially external the user's body and that is in fluid communication with one or more internal systems of the user's body, the wrap comprising:
an annular panel configured to wrap around and cover a user's chest and upper back, the annular panel having first, second, third and fourth end portions, the first end portion disposed generally opposite from the second end portion, the first and second end portions being configured to at least partially overlap each other when the annular panel is wrapped around the user's chest, the third and fourth end portions being configured to at least partially overlap each other adjacent an apex of one of a right shoulder or left shoulder of the user, but not both shoulders simultaneously;
a first fastener disposed on the first end portion and a complementary second fastener disposed on the second end portion, wherein the first and second fasteners are configured to releasably attach to each other;
a third fastener disposed on the third end portion and a complementary fourth fastener disposed on the fourth end portion, wherein the third and fourth fasteners are configured to releasably attach to each other; and
a holder assembly disposed on a lower edge of the annular panel and configured to secure a portion of the tube, the holder assembly including a fabric strip attached to, or formed with, the annular panel, the fabric strip having fifth and sixth end portions and a middle portion disposed between the fifth and sixth end portions, the middle portion being configured to support the portion of the tube, the fifth end portion being attached to, or formed with, the annular panel and having a fifth fastener, and the sixth end portion having a sixth fastener, wherein the fifth and sixth fasteners are configured to releasably attach to each other.

* * * * *